United States Patent [19]

Lentz et al.

[11] Patent Number: 4,585,889
[45] Date of Patent: Apr. 29, 1986

[54] CARBONYLATION PROCESS FOR THE PRODUCTION OF MONOESTERS AROMATIC DICARBOXYLIC ACIDS FROM PHOSPHONIUM SALTS

[75] Inventors: Carl M. Lentz, Mt. Carmel; James R. Overton; David D. Cornell, both of Kingsport, all of Tenn.

[73] Assignee: Eastman Kodak Company, Rochester, N.Y.

[21] Appl. No.: 695,496

[22] Filed: Jan. 28, 1985

[51] Int. Cl.$^4$ ............................................. C07C 67/36
[52] U.S. Cl. ......................................... 560/90; 560/84; 560/85; 560/86; 560/91; 560/94; 560/97
[58] Field of Search ..................... 560/91, 97, 90, 94, 560/85, 86, 84

[56] References Cited

U.S. PATENT DOCUMENTS 2,640,071  5/1953  Leibu .................................. 560/57
3,988,358  10/1976 Heck .................................. 560/97 X

*Primary Examiner*—Natalie Trousof
*Assistant Examiner*—Vera C. Clarke
*Attorney, Agent, or Firm*—Clyde L. Tootle; J. Frederick Thomsen

[57] ABSTRACT

The present invention provides a process for the preparation of monoesters of dicarboxylic acids by the carbonylation of carboxyphenyl-triarylphosphonium salts. The carboxyphenyl-triarylphosphonium salts are reacted with carbon monoxide and an alcohol in a base reaction medium having a $pK_b$ greater than about 8.

9 Claims, No Drawings

CARBONYLATION PROCESS FOR THE PRODUCTION OF MONOESTERS AROMATIC DICARBOXYLIC ACIDS FROM PHOSPHONIUM SALTS

DESCRIPTION

This invention relates to a novel carbonylation process for the production of monoesters of dicarboxylic acids. More particularly, this invention relates to a novel process for the carbonylation of a carboxyphenyl-triaryl phosphonium salt in the presence of an alcohol in a base reaction medium having a $pK_b$ greater than about 8.

The preparation of carboxylic acid esters by carbonylation process is well known in the art. One such process is described in U.S. Pat. No. 3,988,358 whereby carboxylic acid esters or amides are obtained from aryl halides and substituted derivatives thereof by the reaction of the particular starting material with an alcohol or primary or secondary amine and carbon monoxide in the presence of a palladium catalyst.

Generally, in the other carbonylation processes known in the prior art it is necessary that a noble metal be used as a catalyst in the process. However, a carbonylation process which does not require a noble metal catalyst is described in Davidson et al (*J. Chem. Soc. (A)*, 1968, pp. 1616–17) which discloses the reaction of diphenyliodonium bromide and carbon monoxide at 190 atmospheres in methanol at 100° C. in the absence of a catalyst. However, without a catalyst the process only provided methylbenzoate in yields of about 35 to 50%.

Therefore, it would be an advance in the state of the art to provide a carbonylation process to prepare organic aromatic monoesters of dicarboxylic acids in high yields without a noble metal catalyst.

In accordance with the present invention, it has now been found that the carboxyphenyl-triaryl phosphonium salt can be carbonylated to the monoesters of dicarboxylic acids by reaction with carbon monoxide and an aliphatic alcohol in a base reaction medium.

The carboxyphenyl-triaryl phosphonium salt employed as a starting material in the process of the present invention has the following chemical formula:

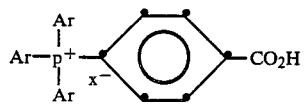

wherein Ar is a phenyl group and x is a halogen.

The carboxyphenyl-triaryl phosphonium salts employed in the process of the present invention can be prepared by the methods described by *Bull. Chem. Soc. Jpn.* (1983) 56 2869, the disclosure of which is incorporated herein by reference in its entirety.

The carboxyphenyl-triaryl phosphonium salt is reacted with an aliphatic alcohol having up to about 12 carbon atoms in the presence of carbon monoxide, and in a base reaction medium having a $pK_b$ greater than about 8, preferably about 8.0 to about 11.0, most preferably about 9.0 to about 10.0.

More particularly, the monoesters of aromatic dicarboxylic acids are produced by the reaction of a carboxyphenyl-triaryl phosphonium salt with an aliphatic or aromatic alcohol. The aliphatic or aromatic alcohol which is employed in the present process may be monofunctional or multifunctional. Therefore, glycols and other polyols are suitable, as are glycol esters, glycol ethers, and other such derivatives. Preferably, the alcohol comprises a lower alkanol such as an alkanol having up to about 12 carbon atoms, ethylene glycol, propylene glycol, neopentyl glycol, ethylene glycol monoacetate, mixtures thereof, and the like.

The catalytic carbonylation reaction of the present invention is conducted in the presence of carbon monoxide, which is employed in amounts such that the total reaction pressure is in the range of atmospheric pressure to about 500 psig (about 3500 kPa). Superatmospheric pressure may be advantageous when a volatile reactant is employed or when an increase in the rate of reaction is desirable. Pressures from 100 pressure up to about 200 psig (about 1750 kPa) are most preferred.

The process of the present invention can be conducted at temperatures of about 50° C. to about 200° C. Preferably, the temperature of the reaction is in the range of about 75° C. to 100° C., most preferably 80° C.

The reaction is carried out in a reaction medium having a $pK_b$ greater than about 8.0, preferably about 8.0 to about 11.0. The base used can be an organic base or an inorganic base. The base is present in an amount of about 1 mole carboxyphenyltriaryl phosphonium salt to 1 mole base to about 1 mole carboxyphenyl-triaryl phosphonium salt to 10 mole base which provides a reaction medium having a $pK_b$ of at least 8, preferably about 1 mole carboxyphenyltriaryl phosphonium salt to 3 moles base. Bases which have been particularly useful are inorganic bases such as, for example, sodium hydroxide, potassium hydroxide, sodium carbonate, and the like. Organic bases which are particularly useful are, for example, trialkyl amines such as trimethylamine, triethylamine, tributylamine, triphenylamine, and the like.

Inert coordinating solvents may be employed, but are not necessary. Such solvents include, for example, tetrahydrofuran, acetonitrile, and the like. In preparing monoesters of dicarboxylic acids by the reaction of a carboxyphenyl-triaryl phosphonium salt with carbon monoxide and an alcohol, the alcohol can be employed as solvent.

The process of the present invention provides an efficient, novel and economical process for providing products which are useful as intermediates in the synthesis of polyesters, such as polyethylene terephthalate, and other useful polymeric materials.

The invention will be further illustrated by the following Examples although it will be understood that these Examples are included merely for purposes of illustration and are not intended to limit the scope of the invention.

Examples 1–10

The following Examples illustrate the carbonylation of a triphenyl-p-carboxyphenylphosphonium halide salt in the presence of an alcohol, a base and carbon monoxide to produce the corresponding alkyl hydrogen terephthalate. The particular halide, alcohol, base employed in each example are indicated below in Table I. The base was present in a concentration of 3.0 millimoles per millimole of triphenyl-p-carboxyphenylphosphonium halide salt.

In each Example, a laboratory autoclave was fitted with a reflux condenser, a thermometer, magnetic stirrer, and a gas dispersion tube. To the described apparatus were added 2 millimoles of triphenyl-p-carboxyphenylphosphonium hadide salt, 6 millimoles of the indicated base, and 70 ml of the indicated alcohol. While carbon monoxide was fed beneath the surface of the reaction mixture at the indicated total pressure, the reaction mixture was heated to the indicated temperature and was held at that temperature for the indicated period of time. The resulting mixture was cooled to 25° to 30° C. and poured into 200 ml of water. The pH was adjusted to 2 with 32% aqueous hydrochloric acid. The resulting mixture was extracted three times with 50 ml of dichloromethane. The extracts were combined and washed with 100 ml of water and then dried over magnesium sulfate. The solvent was removed in vacuo. GLPC analysis, employing authentic samples for comparisons, established the composition of the product.

The results of these Examples are given in Table I.

TABLE I

| Ex. | X | Alcohol | Temperature (°C.) | Pressure (psig) | Base | Conversion (%) | Time (hrs) |
|---|---|---|---|---|---|---|---|
| 1 | $I^-$ | Methanol | 50 | 100 | $Et_3N$ | 86.1 | 4 |
| 2 | $I^-$ | Methanol | 80 | 100 | $Et_3N$ | 96 | 4 |
| 3 | $I^-$ | Methanol | 50 | 200 | $Et_3N$ | 72 | 4 |
| 4 | $Br^-$ | Methanol | 50 | 100 | $Et_3N$ | 56 | 4 |
| 5 | $I^-$ | Ethanol | 80 | 100 | NaOH | 61 | 4 |
| 6 | $I^-$ | Ethylene Glycol | 80 | 100 | $Na_2CO_3$ | 85 | 4 |
| 7 | $Cl^-$ | Ethylene Glycol | 80 | 100 | $K_2CO_3$ | 70 | 4 |
| 8 | $I^-$ | Ethylene Glycol Monoacetate | 80 | 100 | $Na_2CO_3$ | 80 | 4 |
| 9 | $I^-$ | Ethanol | 80 | 100 | $Na_2CO_3$ | 56 | 2 |
| 10 | $I^-$ | Methanol | 80 | 100 | $Et_3N$ | 81 | 2 |

Examples 11–13

These Examples demonstrate the advantages of the present invention. In particular, these Examples demonstrate that the tri-phenyl-p-carboxyphenylphosphonium iodide of the above Examples is carbonylated in the presence of a base medium having a $pK_b$ greater than 8, triphenyl amine, but is not carbonylated in the absence of either an acid or a base medium, in the presence of an acid medium, or in the presence of a base medium having a $pK_b$ less than 8, pyridine.

In Example 11 about 1.0 millimole of triphenyl-p-carboxyphenylphosphonium iodide salt and 40 ml of the indicated alcohol and no base or acid were provided to the reaction medium in the above-described reaction apparatus. In Example 12 about 3.0 millimole hydrochloric acid, based on the amount of salt, was added to the reaction medium to provide an acid reaction medium. In Example 13 about 3.0 millimole triphenyl amine, based on the amount of salt, was added to the reaction mixture to provide a base reaction medium having a $pK_b$ greater than 8. In Example 14 about 3.0 millimole of a weak base pyridine, based on weight of salt, was added to the reaction mixture to provide a base reaction medium having a $pK_b$ of less than 8. While carbon monoxide was fed beneath the surface of the reaction mixture so that the indicated total pressure was obtained, the reaction mixture was heated to the indicated temperature and was held at that temperature for the indicated period of time. Upon completion of reaction, the reaction mixture was worked up as described above. The results are given below in Table II.

TABLE II

| Ex. | Alcohol | Added | Temperature (°C.) | Pressure (psig) | Conversion (%) | Time (hrs) |
|---|---|---|---|---|---|---|
| 11 | Methanol | Nothing | 50 | 100 | 0 | 2 |
| 12 | Methanol | HCl | 50 | 100 | 0 | 2 |
| 13 | Methanol | triphenylamine | 50 | 100 | 52 | 2 |
| 14 | Methanol | pyridine | 50 | 100 | 0 | 2 |

These results clearly demonstrate that conversion of the carboxyphenyl-triarylphosphonium salt to the corresponding monoester occurred in the presence of the strong base while no reaction occurred in the presence of an acid, a weak base, or without the base.

The invention has been described in detail with particular reference to preferred embodiments thereof, but it will be understood that variations and modification can be effected within the spirit and scope of the invention.

We claim:

1. A process for the preparation of monoesters of aromatic dicarboxylic acids comprising reacting a carboxyphenyl-triaryl phosphonium salt of the formula

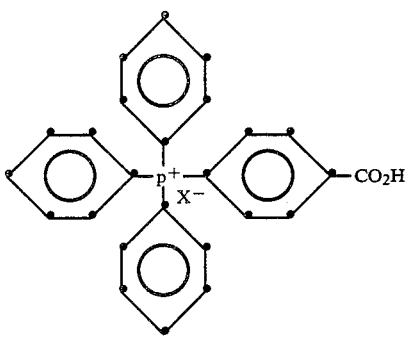

wherein X represents a weak acid anion, with (i) carbon monoxide and (ii) an aliphatic alcohol having up to 12 carbon atoms in a base reaction medium having a $pK_b$ greater than about 8.0.

2. The process of claim 1 wherein said alcohol comprises a lower alkanol, ethylene glycol, propylene glycol, neopentyl glycol, ethylene glycol monoacetate, or a mixture thereof.

3. The process of claim 5 wherein the reaction temperature is about 100° C. to about 700° C.

4. The process of claim 6 wherein the reaction system further comprises a base having a pK$_b$ of about 8.0 to about 11.0.

5. The process of claim 7 wherein said base comprises triethylamine or sodium carbonate.

6. A process for the preparation of monoesters of dicarboxylic acids which comprises reacting at a temperature of about 100° to about 200° C. a salt of the formula

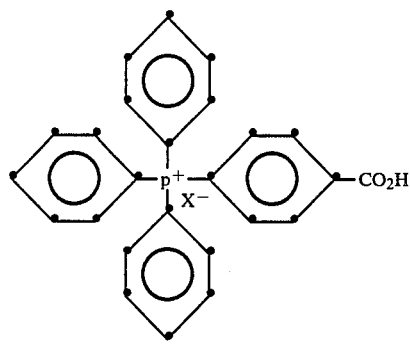

wherein X represents a weak acid anion comprising iodide, bromide, or chlorine, with carbon monoxide and an alcohol comprising an alkanol containing up to 12 carbon atoms, in a base reaction medium having a pK$_b$ of about 9.0 to about 10.0.

7. The process of claim 10 wherein said alcohol comprises methanol, ethanol or a mixture thereof.

8. The process of claim 11 wherein the reaction temperature is about 100° to about 150° C.

9. The process of claim 12 wherein said base comprises triethylamine or sodium carbonate.

* * * * *